United States Patent [19]

Cowsar et al.

[11] 4,181,500
[45] Jan. 1, 1980

[54] CHEMICAL TESTING SYSTEMS

[75] Inventors: Donald R. Cowsar; Steadman D. Harrison, Jr., both of Birmingham, Ala.

[73] Assignee: Burroughs Wellcome Co., Research Triangle Park, N.C.

[21] Appl. No.: 651,424

[22] Filed: Jan. 22, 1976

[51] Int. Cl.² .................... G01N 31/22; G01N 31/16
[52] U.S. Cl. .................... 23/230 B; 23/925; 252/408; 422/58; 422/56
[58] Field of Search .......... 23/253 TP, 230 R, 230 B; 252/408; 422/55, 56, 57, 58

[56] References Cited

U.S. PATENT DOCUMENTS

| | | | |
|---|---|---|---|
| 2,785,057 | 3/1957 | Schwab et al. | 23/253 TP |
| 3,485,587 | 12/1969 | Keston | 23/230 B |
| 3,523,011 | 8/1970 | Bhiwandker et al. | 23/253 TP |
| 3,552,928 | 1/1971 | Fetter | 23/230 B |
| 3,673,183 | 6/1972 | Erickson | 23/253 TP X |
| 3,711,252 | 1/1973 | Roy | 23/253 TP |
| 3,783,105 | 1/1974 | Moyer et al. | 23/253 TP X |
| 3,810,739 | 5/1974 | Nussbaum | 23/253 TP |

OTHER PUBLICATIONS

Larson et al., Anal. Chem. 25,802 (1953).

Primary Examiner—Michael S. Marcus
Attorney, Agent, or Firm—Donald Brown

[57] ABSTRACT

A test system and method is described for determining if a material (e.g. uric acid) oxidizable by iodine is present in an aqueous fluid in an amount equal to or greater than a predetermined amount and which includes a dry solid iodine indicator and a dry solid means for rapidly generating iodine in situ upon activation thereof to color said indicator, said system preferably being in test strip form.

As another feature of this invention there is provided a solid source of basic anions capable upon activation of neutralizing excess protons remaining after generating iodine in situ to permit rapid oxidation of the material oxidizable by said iodine without substantially interfering with the rapid generation of said iodine.

23 Claims, 4 Drawing Figures

CHEMICAL TESTING SYSTEMS

BACKGROUND OF THE DISCLOSURE

This invention relates to chemical testing systems and in particular is an improvement in such systems which provide visible color reactions inversely proportional to the amount of material reacting therewith. The system herein is particularly suitable for rapidly determining if a material oxidizable by iodine such as uric acid is present in an aqueous solution in an amount greater than a predetermined amount.

The present invention is particularly suitable for use in strip form to determine if the quantity of uric acid present in bodily fluids such as blood, urine, saliva, etc. is present in such fluids in more than normal amounts.

As is well known, excess uric acid in humans may cause deposits of same to accumulate in the joints and kidneys. Often patients are unaware of excess uric acid in their bodies. While tests are available for making determinations of uric acid in body fluids, they are in general not readily acceptable for use by physicians in their officies. Accordingly, there has developed a demand for a new and improved testing system for uric acid determinations which could be readily usable by physicians in their offices to screen patients to determine which patients should be further evaluated.

Thus the purpose of this invention is to provide such a test system suitable for use by physicians as part of their regular in office examinations.

BRIEF DESCRIPTION OF THE DISCLOSURE

The present invention in its preferred form includes a water activatable solid iodine-generator for rapidly generating iodine in situ to color an iodine indicator and a water activatable solid source of basic anions to neutralize the protons remaining after the generation of the iodine whereby the released iodine and uric acid may react together under alkaline conditions to cause said indicator to lose its color if the amount of uric acid present is greater than a predetermined amount. The present invention provides a system in which the iodine-generator is stable over a prolonged period of time and iodine is not released prior to activation of the source thereby preventing a loss in quantitative accuracy which would occur if a direct source of iodine such as an iodophor was used.

In the preferred form of the invention the generation of iodine is substantially completed in a rapid manner, e.g. preferably within one to two minutes, after activation by wetting the solid iodine generator with an aqueous solution, e.g., plasma or serum from blood.

Since activation occurs in part by the formation of an acid solution the overall solution takes on an acidic pH. Initially it was found that if the solution was acidic, the rapid reaction of iodine with uric acid to provide the desired color change was prevented. As a solution to this problem it has been found that if a delayed and sequential reversal of acidity is effected by the activation of a basic anion source, iodine could still be rapidly generated without prematurely neutralizing the acid reactants and thereafter it was still possible to achieve a rapid color change, i.e. purple or blue to colorless, if more than a predetermined amount of uric acid was present in the blood, urine, etc., in 1 to 2 minutes after initiation of the reactions noted above. It has also been unexpectedly found that the present invention is capable of being practiced using a solid impregnated matrix for all or at least some of the reactants used. Thus, in the most preferred form of this invention, it is possible to use a layer of solid material impregnated with a source of base, a color indicator, and at least some of the means for generating the iodine which is then activated to produce iodine by the wetting thereof by water from blood, urine, etc. It has also been unexpectedly found that the use of the solid impregnated material does not prevent the desired sequential reactions from being controllable, i.e. (1) the formation of $I_2$ under acidic conditions, (2) the change of pH to basic after generation of $I_2$ by neutralizing the solution in the matrix and then (3) the generation of urate ions frm uric acid which react with $I_2$ to alter the color of the color indicator initially colored purple or blue by $I_2$ (iodine) complexing with starch or the like if the concentration of urate ions is greater than a predetermined amount.

DETAILED DESCRIPTION OF THE DISCLOSURE

Figure 1:
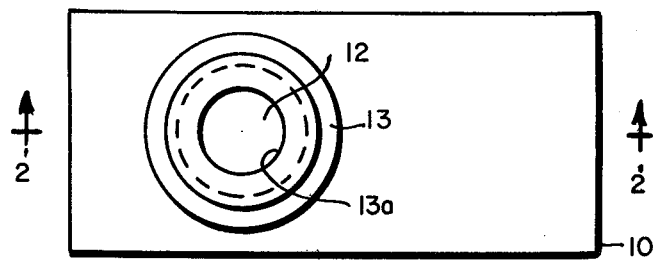
FIG. 1 is a top view of a test strip according to the disclosure.
Figure 2:
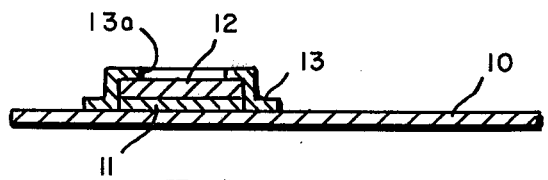
FIG. 2 is a sectional view taken along line 2—2 in FIG. 1.

Reference should now be had to FIGS. 1 and 2 for a description of the preferred embodiment of the disclosure. At 10 there is shown a base layer of an inert material preferably optically clear such as polycarbonate, polyvinyl chloride, polypropylene, glass, polymethylmethacrylate, polyesters, e.g. Mylar ®, polyamides such as nylon, etc. A suitable thickness of the material, e.g. if Mylar, would be about 20 mils to preferably provide the stiffness for easy handling by the user. At 11 there is shown an impregnated colorless layer of material comprising (1) an inert colorless support such as cellulose filter paper, e.g. Whatman #1, obtainable from scientific supply companies or glass fibre filter material such as GFC/C Whatman, or other inert absorbing materials such as cotton, polyester, etc., well known to those skilled in the art; (2) a portion of an iodine-generator comprising an ammonium or alkali metal iodide and an ammonium or alkali metal iodate both in solid particulate form; (3) a color indicator, e.g. an iodine indicator such as starch particles, which forms a complex with iodine to provide a deep blue or purple color. Alternative iodine indicators that may also be used are amylase or amylopectin, dextrin, α-naphthaflavone, polyvinylpyrrolidone, polyvinyl alcohol, glycogen, sodium starch glycollate or other polysaccharides which give a satisfactory color reaction with iodine. The amount of color indicator should be in excess with respect to the total amount of potentially available iodine in the composition to insure that all iodine generated is consumed in forming the highly colored iodine-indicator complex, e.g. iodine-starch complex; (4) a source of basic anions in solid particulate form (a) of the type having low solubility in water, e.g. alkaline earth hydroxide and alkaline earth carbonates such as calcium carbonate, barium carbonate, strontium carbonate, magnesium carbonate, calcium hydroxide, barium hydroxide, strontium hydroxide, and magnesium hydroxide, or (b) as an encapsulated source of basic anions such as the aforementioned bases or other bases such as alkali metal hydroxides, bicarbonates, carbonates, e.g. sodium hydroxide, sodium carbonate, sodium bicarbonate, potassium hydroxide, potassium carbonate, potassium bicarbonate, etc., the bases wall preferably being in solid particulte form and encapsulated in a water soluble shell such as hydroxyethyl cellulose, gelatin, starch, etc.

The diameter of the layer 11 is conveniently about 4 to 10 mm with about 6 mm diameter being preferred. The dimensions of the layer 11 are selected so that said layer will preferably saturate with about 1 drop of blood (i.e., 1/20 ml) or 30 mg blood serum. The thickness of the layer may conveniently be about 0.16 mm for Whatman #1 filter paper. The layer 11 is conveniently prepared by forming a solution of the indicator, e.g. starch, the basic anion source, the iodide salt and the iodate salt in an aqueous solvent such as water. The filter paper is then conveniently dipped in the solution for 10 to 15 seconds and the solvent is allowed to evaporate leaving the impregnated filter paper.

At 12 there is shown a porous layer comprising a tissue paper impregnated with an acid source for providing the protons required for the generation of $I_2$ when combined with the iodide and iodate salts. The tissue paper may conveniently be selected from Kimwipes® (Kimberly Clark), Kleenex®, U.S. Toilet tissue (Scott), etc. or thinner filter papers of the type mentioned for layer 11. The tissue paper because of its porosity is easily impregnated with the acid source and conveniently rapidly releases acid upon wetting thereof by water, as from blood.

The acids used preferably have low acid neutralization equivalents of less than 100 although up to 200 is quite acceptable. The particular acids are selected as above to provide an adequate source of protons from a minimal weight of the solid acid.

Acids particularly suitable include oxalic (neutralization equivalent 45) maleic, fumaric, polymethacrylic acid, p-toluene sulphonic acid, benzoic acid, boric acid, etc., all well known to those skilled in the art. The paper selected is most conveniently Kimwipes 0.07 mm thick with diameter of about 4 to 10 mm and 6 mm being most preferred. The paper is impregnated by forming an aqueous acid solution and then dipping the paper into the solution, e.g. 3 to 10 seconds, to saturate same. Thereafter the paper is allowed to dry.

The actual test strip preparation is based on the amount of liquid, e.g. urine, serum, plasma, etc., which the solid, impregnated matrix contains when it is saturated. For example, if a suitable absorbent paper matrix holds when saturated 1.6 ml of water per sheet 10 cm $\times$ 10 cm, a circular disc of the same material 6 mm in diameter would hold about 0.0045 ml.

An aqueous liquid, e.g. serum, containing 7 mg percent (i.e. 7 mg/100 ml) of uric acid would contain about 0.0003 mg of uric acid in 0.0045 ml (0.0045/100$\times$7). This is equivalent to $1.87\times10^{-9}$ mole of uric acid. The reaction employed in the test strip system is the oxidation of uric acid by iodine according to the reaction:

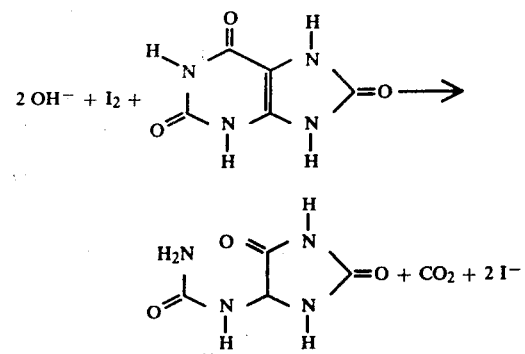

Thus, one mole of iodine is required to oxidize one mole of uric acid; so for $1.87\times10^{-9}$ mole of uric acid, $1.87\times10^{-9}$ mole of iodine is required.

In the preferred system of this invention iodine is generated in situ at the time of the test preferably according to the reaction:

$$6H^+ + 5I^- + IO_3^- \rightarrow 3I_2 + 3H_2O$$

Thus the generation of one mole of iodine requires 5/3 moles of an iodide salt, ⅓ mole of an iodate salt, and 2 moles of protons.

In order for $1.87\times10^{-9}$ mole of iodine to be generated on the test strip, the solid matrix disc must, therefore, be impregnated with $3.1\times10^{-9}$ mole of an iodide salt ($5.1\times10^{-4}$ mg of potassium iodide, for example), $6.2\times10^{-10}$ mole of an iodate salt (e.g., $1.3\times10^{-4}$ mg of potassium iodate). At least $3.74\times10^{-9}$ mole and preferably a slight excess of protons must also be provided, preferably from a rapidly dissolving solid acid impregnated on a thin matrix such as tissue paper (e.g. this would be provided by at least $1.7\times10^{-4}$ mg, preferably about $2.0\times10^{-4}$ mg, of oxalic acid). The test strip should be so constructed that liquid applied to it passes first through the acid-impregnated tissue and then on to the iodide-iodate-impregnated paper disc.

The iodide-iodate-impregnated disc should also contain dispersed therein a sufficient amount of a color indicator such as and preferably starch to form a colored complex with the iodine generated. It should also contain a slowly soluble source of basic anions to provide a means for neutralizing the excess protons after the generation of iodine is complete and also to provide sufficient hydroxyl ions to permit the oxidation of uric acid by the iodine so generated. Thus, the oxidation of $1.87\times10^{-9}$ mole of uric acid by iodine requires $3.74\times10^{-9}$ mole plugs an amount equivalent to the amount of excess protons (e.g. $0.75\times10^{-9}$ mole if a 20% excess of the acid is used) i.e. a total of at least about $4.5\times10^{-6}$ mole of hydroxyl ions and preferrably about $5.5\times10^{-9}$ mole should be present in the iodide-iodate-impregnated disc.

When the test system is designed for use in testing whole blood, e.g. from a finger prick, in order to minimize interference in reading the test strip results, it is desirable that the red blood cells be excluded in some way, e.g. by using the serum expressed during clotting, by using the serum or plasma separated by centrifugation in a microhematocrit determination, etc.

In order to retain the layers 11 and 12 on the layer 10 there is provided a pressure sensitive tape layer 13, e.g., masking or cellophane tape, e.g. made by Professional Tape Co., Inc. (TIME ® TAPE) or by 3M, respectively, and which is provided with a hole 13a so that fluid may be applied to the layer 12.

In use aqueous uric acid, e.g., blood plasma or serum, is placed on the layer 12 e.g. by dropper through the hole 13a.

Figure 3:
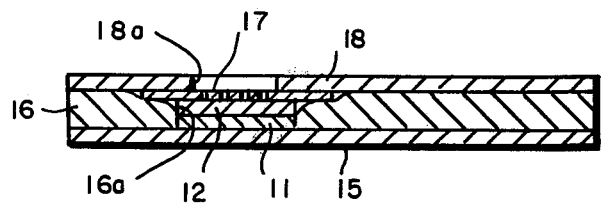
FIG. 3 is a sectional view similar to FIG. 2 showing the use of a semipermeable membrane according to the disclosure and a tear apart test strip.

Reference should now be had to FIG. 3 which shows a modification of the test strip of the invention.

The parts 11 and 12 are the same as described with respect to FIGS. 1 and 2. At 18 is there is shown a PVC (polyvinyl chloride) support layer having an opening 18a acting as a well for fluid (e.g., blood) containing uric acid.

Positioned below the layer 18 is a semi-permeable membrane 17 such as Nuclepore or Millipore ® membrane which is suitable for passing water and uric acid onto the layer positioned below it, while at the same time acting as a filter for red blood cells.

Suitable pore size for the Nucleopore membrane is about 0.8 to 1.0 microns although obviously this will vary depending on the fluid to be tested. Obviously other semi-permeable membranes well known in the art may also be used.

A conventional cellophane layer 16 having an adhesive coating, e.g., Scotch Tape, and having a well hole 16a cut out therefrom is then provided. The layer 16 holds the membrane 17 against the layer 18 and provides the well hole for positioning layers 12 and 11 as shown.

Below the layer 16 there is provided conventional tear tape layer 15 such as masking tape, e.g., made by Minnesota Manufacturing Mining Co. (3M).

The tear tape has the layer 11 adhesively attached to it and is also adhesively attached to the bottom (non-adhesive side) of layer 16.

In use, blood would be placed in the well above layer 17. Water and uric would then pass through the layer 17 used to separate red blood cells therefrom. Thereafter the reactions set forth above for layers 12 and 11 would take place. After a period of time, e.g., 2 minutes, the tear tape is pulled away from the layer 16 and carries the layer 11 therewith so that its color may be observed to determine if the concentration of uric acid in the fluid is above (colorless or white) or below (purple or blue) a predetermined amount.

Figure 4:
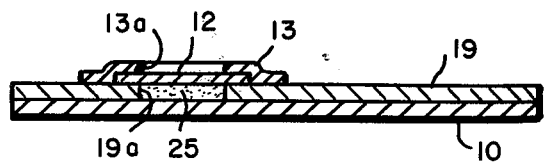
FIG. 4 is a sectional view similar to FIG. 2 showing a well for retaining the activatable ingredients and color indicator.

FIG. 4 illustrates yet another embodiment of the disclosure. In this embodiment, the layer 10 is the same as that shown in FIGS. 1 and 2 and may for example be Mylar. A layer 19 provided with a hole 19a is attached by gluing same to the layer 10. The layer 19 may also be Mylar or other materials as specified above for layer 10.

Positioned above the layer 19 is the acid impregnated layer 12 as disclosed in relationship to FIGS. 1 and 2 which is held against the layer 19 by the pressure sensitive layer 13 having a hole 13a as disclosed with respect to FIGS. 1 and 2.

In this figure a dry solid particulate mixture of the color indicator, e.g., starch, the iodide salt, the iodate salt and the basic anion source are placed at 25 in the well defined by the hole 19a.

The mixture may conventionally be prepared by mixing dry particles of each of the ingredients used to impregnate layer 12 in a dry state, in a mortar and using a pestle to crush same to preferably form a homogeneous dry mixture.

Conveniently a diluent, e.g., cellulose, may be incorporated in the mixture.

From the above it should be realized by those skilled in the art that the precise amounts of the ingredients in the mixture 25 or the layer 11 and the amount of acid impregnated in layer 12 will vary depending upon the level of uric acid to be detected. Accordingly, it should be understood by those skilled in the art the amounts given above are merely illustrative and are not considered as limiting.

The test system of this invention can conveniently be used for the diagnosis of gout in which the amount of uric acid in the blood serum or blood plasma is greater than a predetermined normal amount, e.g., 6 mg/100 ml for females or 7 mg/100 ml for males.

The present invention provides advantages over the prior use of an iodophor as a source of iodine in that, because of the nature of the ingredients used, accuracy of the test system is assured for a prolonged period of time since the shelf life of the ingredients is indefinite and no iodine is generated until water is applied to the test system.

When an iodophor is used the iodine is continually generated and thus continues to evaporate until used. The evaporation of iodine obviously affects the accuracy of the prior art test systems.

This invention also provides for a reversal in acidity after formation of iodine by providing a slowly liberated source of base which converts the solution to alkaline from acidic after generation of $I_2$, e.g., from a pH of 3 to about 7+, to provide the alkaline conditions necessary for the rapid reaction of urate ions and iodine.

It has been found that a reversal of acidity is possible as noted above without substantially affecting the generation of iodine ($I_2$). It has also been unexpectedly found that the reactions noted above as taking place in the layer 12 do in fact take place in a solid impregnated matrix using a back titration technique in the absence of large volumes of solvent.

Thus, in one aspect this invention provides in a test system aqueous activatable means for generating iodine in situ in the presence of a color indicator.

In another aspect this invention provides means at the situs for reversing the acidity of the solution of $I_2$ formed, i.e., from acidic to basic, to permit rapid reaction of urate ions and iodine without substantially effecting the formation of $I_2$.

In yet an additional aspect this invention provides activatable means for generating acid which is then permitted to mix with other activatable ingredients in order to generate iodine.

In a further aspect of this invention there is provided a system for detecting the presence of a greater or less than a predetermined amount of urate ions in an aqueous system by providing the ability to observe the color exhibited by a color indicator colorable by iodine.

Example 1. Test Strip for Detecting Uric Acid

Solution A (starch-iodide-iodate-base). Soluble starch (1.0 g reagent grade, Merck and Co.) was added to water (10 ml) and the resulting suspension added to boiling water (80 ml). The solution was heated at boiling for several minutes and then diluted to 100 ml. To this solution was added 50 ml of a solution of potassium iodate (prepared from 0.118 g of $KIO_3$ in one liter of water) which also contained magnesium carbonate (0.0405 g) and potassium iodide (3.0 g). The resulting mixture was then diluted to 200 ml.

Solution B (acid source). Oxalic (0.25 g) was dissolved in water and the solution diluted to 100 ml.

I. Preparation of Test Papers

Filter paper (Whatman, No. 1, 0.16 mm thick) was dipped in solution A for 10 seconds and then dried. Discs (6.0 mm diameter) were punched out of the dried, impregnated filter paper. These were stored in a bottle in the presence of a desiccant until used. Absorbent tissues (Kimwipes ®, 0.06 mm thickness) were dipped in solution B for 10 seconds and allowed to dry.

II. Assembly of Test Strips

A hole (about 3.0 mm diameter) was punched in a section of Time ® pressure sensitive adhesive tape. A disc (6.0 mm diameter) of the acid-impregnated tissue was placed over the hole on the adhesive side of the tape. Then a disc (6.0 mm diameter) of the starch-iodide-iodate-base-impregnated paper was placed over the acid-impregnated disc. A polycarbonate backing film (0.39 mm thick) was placed over the tape and discs and firmly pressed onto the adhesive tape.

III. Use of the Test Strip

One to about three drops of an aqueous uric acid solution containing 8 mg of uric acid per 100 ml is dropped onto the well of the test strip. The test paper will then turn dark blue within about 30 seconds. Since the uric acid concentration of the solution is greater than 7 mg%, the test strip disc turns from blue to white in 2-5 minutes.

Example 2. Test Strip

A test strip was made according to Example 1 except that a disc (6.0 mm diameter) of a semi-permeable membrane (Nuclepore ® N080, 0.8$\mu$ pore diameter, 10$\mu$ thick, $3 \times 10^7$ pores/cm$^2$) was applied over the hole in the Time ® pressure sensitive tape before the two impregnated discs were attached.

Example 3. Test Strip

A test strip was prepared as in Example 2 except that polyacrylic acid was the acid source rather than oxalic acid. An aqueous solution of polyacrylic acid was coated onto the backside (i.e., the side not attached to the pressure sensitive tape) of the Nuclepore ® membrane and allowed to dry before fabrication of the test strip. The oxalic acid impregnated paper was omitted in this test strip.

Example 4. Test Strip

A test strip is prepared as in Example 1 except that an equimolar amount of calcium carbonate is used in place of magnesium carbonate.

As used herein the term an effective amount of iodine means an amount of iodine effective to provide a color change indication if uric acid or the like is present in an aqueous solution in more than about a predetermined concentration. Reference may be had to the above explanation which provides those skilled in the art the means to calculate the amount of iodine necessary to indicate different levels of uric acid or the like in aqueous solution.

I claim:

1. A test strip for determining if a material oxidizable by iodine is present in an aqueous solution in an amount greater than a predetermined amount, comprising support material having impregnated therethrough at least a portion of water activatable generator means in solid dry form for generating an effective amount of iodine in situ and color indicator means for indicating the presence of iodine, said means for generating iodine comprises an iodide salt, an iodate salt and an acid, and a source of basic anions in dry solid form for neutralizing protons formed during generation of said iodine.

2. The test strip of claim 1 including means defining a well for at least a portion of said generator, indicator and source means.

3. The test strip of claim 1 in which the indicator means is starch.

4. The test strip of claim 1 in which the system includes means to separate red blood cells from said indicator.

5. The test strip of claim 1 wherein said indicator, said iodide salt and said iodate salt are impregnated in an absorbent material.

6. The test strip of claim 5 in which said source of basic anions is impregnated in said absorbent material.

7. The test strip of claim 6 in which said acid is impregnated in a porous material which is in physical contact with said absorbent material whereby said aqueous solution passing through the acid impregnated porous material will cause the flow of acid into said absorbent material to initiate the generation of iodine in situ.

8. A test strip comprising a first inert layer having means for the receipt of fluid, a porous layer positioned under said means and supporting acid in solid dry form, an absorbent layer positioned below said porous layer and in intimate contact therewith, said absorbent layer impregnated with a source of basic anions, a color indicator, an iodate salt and an iodide salt, said acid, iodate salt and iodide salt being present in an amount to generate an effective amount of iodine.

9. The test strip of claim 8 in which said inert layer is clear.

10. The test strip of claim 8 in which the indicator means is starch.

11. The test strip of claim 8 in which said first inert layer includes a filter to separate red blood cells from said indicator.

12. The test strip of claim 8 in which the iodine is first substantially entirely generable prior to said basic source providing substantial amounts of basic anions.

13. A test strip comprising a porous first layer supporting acid in solid particulate dry form, a second layer coupled to said porous layer, said second layer supporting an acid activatable iodine source in solid particulate dry form, a source of basic anions in solid particulate dry form and an iodine indicator in solid particulate dry form, said acid and said acid activatable source of iodine being present in an amount to generate an effective amount of iodine and said source of basic anions being present in an amount sufficient to reverse the pH from acid to alkaline after generation of iodine.

14. The test strip of claim 13 in which said second layer is of absorbent material.

15. The test strip of claim 13 in which the acid activatable iodine source comprises an iodide salt and an iodate salt.

16. The test strip of claim 15 in which said acid is impregnated in said first layer and in which said second layer is impregnated with said source of basic anions, said iodine indicator, said iodide salt and said iodate salt.

17. The test strip of claim 13 in which said iodine source comprises a compound containing iodine in a strong covalent bond.

18. A test strip comprising filter means for separating red blood cells from blood, a porous layer positioned under said filter means and supporting acid in solid dry form, an absorbent layer positioned below said porous layer and in intimate contact therewith, said absorbent layer supporting a source of basic anions, a color indicator, an iodate salt and an iodide salt, all in solid dry form, said acid, iodate salt and iodide salt being present in an amount to generate an effective amount of iodine, and an insert layer coupled to said absorbent layer.

19. The test strip of claim 18 in which said inert layer is peelable.

20. The test strip of claim 18 in which said inert layer is clear.

21. The method of determining if the level of a material oxidizable by iodine in an aqueous test fluid is greater than a predetermined amount which comprises applying said test fluid to a test strip comprising an acid, an acid activatable source of iodine comprising an iodide salt and an iodate salt, a source of basic anions in an amount sufficient to reverse the pH from acid to alkaline after the generation of iodine and iodine indicator all dry solid form, and allowing the fluid to react therewith and thereafter observing the color of the indicator.

22. The method of claim 21 in which the iodine indicator is starch.

23. The method of claim 21 in which the material oxidizable by iodine is uric acid.

* * * * *